United States Patent
Nagaraju et al.

(10) Patent No.: US 11,441,149 B2
(45) Date of Patent: Sep. 13, 2022

(54) CRISPR/CAS SYSTEMS FOR C1-FIXING BACTERIA

(71) Applicant: LanzaTech NZ, Inc., Skokie, IL (US)

(72) Inventors: Shilpa Nagaraju, Skokie, IL (US); Michael Koepke, Chicago, IL (US)

(73) Assignee: LanzaTech NZ, Inc., Skokie, IL (US)

( * ) Notice: Subject to any disclaimer, the term of this patent is extended or adjusted under 35 U.S.C. 154(b) by 471 days.

(21) Appl. No.: 15/442,695

(22) Filed: Feb. 26, 2017

(65) Prior Publication Data

US 2017/0247710 A1    Aug. 31, 2017

Related U.S. Application Data

(60) Provisional application No. 62/300,532, filed on Feb. 26, 2016.

(51) Int. Cl.
*C12N 15/74* (2006.01)
*C12N 15/10* (2006.01)

(52) U.S. Cl.
CPC .......... *C12N 15/74* (2013.01); *C12N 15/102* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 2016/0090603 A1* | 3/2016 | Carnes ............... | C12N 15/8206 800/278 |
| 2016/0289659 A1* | 10/2016 | Doudna ................. | C12N 9/22 |
| 2017/0369866 A1* | 12/2017 | Frisch .................. | C12N 15/102 |

FOREIGN PATENT DOCUMENTS

| | | | |
|---|---|---|---|
| WO | 2015054507 A1 | | 4/2015 |
| WO | PCT/GB2015/051153 | * | 4/2015 |
| WO | 2015089277 A1 | | 6/2015 |
| WO | 2015159087 A1 | | 10/2015 |

OTHER PUBLICATIONS

Nagaraju et al. "Genome editing of Clostridium autoethanogenum using CRISPR/Cas9" 9:219 Biotechnology for Biofuels 1-8 (Year: 2016).*
Cong, Science, 339: 819-823, 2013.
Drake, Acetogenic Prokaryotes, In: The Prokaryotes, 3rd edition, p. 354, New York, NY, 2006.
Jinek, Science, 337: 816-821, 2012.
Mali, Science, 339: 823-826, 2013.
Marraffini, Nature, 526: 55-61, 2015.
Ragsdale, Biochim Biophys Acta, 1784: 1873-1898, 2008.
Travis, Science, 350:1456-1457, 2015.
Wang, J Biotechnol, 200: 1-5, 2015.
Xu, Appl Environ Microbiol, 81:4423-4431, 2015.
Brown et al., "Comparison of single-molecule sequencing and hybrid approaches for finishing the genome of Clostridium autoethanogenum and analysis of CRISPR systems in industrial relevant Clostridia," Biotechnology for Biofuels, 7:40, 2014.
Sander & Joung, "CRISPR-Cas systems for editing, regulation and targeting," Nature Biotechnology, 32(4): 347-355, 2014.
Search Report for European Patent Application No. 17757399.5 dated Jul. 17, 2019, European Patent Office.
Tao, Xu et al., Efficient Genome Editing in Clostridium cellulolyticum via CRISPR-Cas9 Nickase, Applied and Environmental Microbiology, vol. 81, No. 13, Jul. 1, 2015, pp. 4423-4431.
Wang, Yi et al., Markerless chromosomal gene deletion in Clostridium beijerinckii using CRISPR/Cas9 system, Journal of Biotechnology, vol. 200, No. 11, Feb. 2015, pp. 1-5.
Nagaraju, Shilpa et al., Genome editing of Clostridium autoethanogenum using CRISPR/Cas9, Biotechnology for Biofuels, vol. 9, No. 219, 2016, pp. 1-8.
Examinination Report for European Patent Application 17757399.5, European Patent Office, dated Jul. 3, 2020.
Whitham, Identifying Genetic Targets and Growth Conditions for Higher Ethanol Production by the Synthesis Gas Fermenting Bacterium Clostridium Ijungdahlii, Dec. 1, 2015.
Yang Fa-yu et al., Progress of Next-generation Targeted Gene-editing Techniques, China Biotechnology, 2014, 34 (2): 98-113 (with English Abstract).

* cited by examiner

*Primary Examiner* — Nancy J Leith
(74) *Attorney, Agent, or Firm* — Stephen M. Chong

(57) ABSTRACT

The invention provides methods of genetically engineering a C1-fixing bacterium using a Clustered Regularly Interspaced Short Palindromic Repeats (CRISPR)/CRISPR-associated (Cas) (CRISPR/Cas) system. Preferably, the Cas protein is under the control of an inducible promoter.

16 Claims, 5 Drawing Sheets

CRISPR/CAS SYSTEMS FOR C1-FIXING BACTERIA

CROSS REFERENCE TO RELATED APPLICATIONS

This application claims the benefit of U.S. Provisional Patent Application 62/300,532 filed Feb. 26, 2016, the entirety of which is incorporated herein by reference.

BACKGROUND OF THE INVENTION

Prokaryotes have evolved clustered regularly interspaced short palindromic repeats (CRISPR) an adaptive immune system to combat infection by pathogens, such as viruses or other extracellular nucleic acids (Marraffini, *Nature*, 526: 55-61, 2015). When prokaryotes encounter a source of foreign nucleic acid, such as from a virus, they can copy and incorporate segments of the virus into their genome as "spacers" between short palindromic repeat sequences in CRISPR. In the event of re-exposure, CRISPR spacers allow for the rapid identification of the virus and CRISPR repeats guide specialized CRISPR-associated (Cas) enzymes to the site, where they splice and disable the viral nucleic acid.

In the last several years CRISPR/Cas systems have been exploited for a wide range of applications in medicine and biotechnology (see, e.g., U.S. Pat. No. 8,697,359; Travis, *Science*, 350: 1456-1456, 2015; Jinek, *Science*, 337: 816-821, 2012). There remains a need, however, for CRISPR/Cas systems optimized for the genetic modification of industrially-relevant microorganisms, such as C1-fixing bacteria.

SUMMARY OF THE INVENTION

The invention provides methods of genetically engineering a C1-fixing bacterium using a CRISPR/Cas system. In particular, the method involves introducing into a C1-fixing bacterium containing a DNA molecule comprising a target sequence an engineered, non-naturally occurring CRISPR/Cas system comprising one or more vectors comprising (a) a nucleotide sequence encoding a guide RNA that hybridizes with the target sequence and (b) a nucleotide sequence encoding a type-II Cas9 protein under the control of an inducible promoter. The CRISPR/Cas system may further comprise on the one or more vectors (c) a nucleotide sequence comprising a 5' homology arm that hybridizes upstream of the target sequence and a 3' homology arm that hybridizes downstream of the target sequence, whereby the 5' homology arm and the 3' homology arm hybridize with the DNA molecule and homologous recombination occurs, resulting in the replacement of the target sequence with DNA located between the 5' homology arm and the 3' homology arm. These elements may be located on the same or different vectors.

Different types of Cas9 may be used. For example, catalytically active Cas9, including variants such as nickase Cas9, may be used to cleave the DNA molecule. As another example, catalytically inactive Cas9 may be used to block/silence, but not cleave, the DNA molecule.

The CRISPR/Cas system has a wide variety of applications, e.g., deleting, inserting, translocating, inactivating, or activating DNA.

The CRISPR/Cas system may be used to decrease expression of a gene, via cleavage of the gene, insertion of additional DNA into the gene, or silencing/blocking of the gene. In one embodiment, Cas9 cleaves the DNA molecule in a region encoding a gene, whereby expression of the gene is decreased. In another embodiment, Cas9 blocks the DNA molecule in a region encoding a gene, whereby expression of the gene is decreased. In a further embodiment, DNA located between the 5' homology arm and the 3' homology arm disrupts the DNA molecule in a region encoding a gene, whereby expression of the gene is decreased.

Alternatively or additionally, the CRISPR/Cas system may be used to express an exogenous gene. In one embodiment, DNA located between the 5' homology arm and the 3' homology arm encodes an exogenous gene, whereby the homologous recombination inserts the exogenous gene into the DNA molecule. The C1-fixing bacterium may then express the exogenous gene.

In certain embodiments, CRISPR/Cas system is derived from *Streptococcus pyogenes* or *Streptococcus thermophilus*.

The CRISPR/Cas system comprises Cas9 protein under the control of an inducible promoter. This inducible promoter may be, for example, a tetracycline inducible promoter, such as tet3no or ipl12, or a lactose inducible promoter.

Typically, the C1-fixing bacterium is selected from the group consisting of *Acetobacterium woodii*, *Alkalibaculum bacchii*, *Blautia producta*, *Butyribacterium methylotrophicum*, *Clostridium aceticum*, *Clostridium autoethanogenum*, *Clostridium carboxidivorans*, *Clostridium coskatii*, *Clostridium drakei*, *Clostridium formicoaceticum*, *Clostridium ljungdahlii*, *Clostridium magnum*, *Clostridium ragsdalei*, *Clostridium scatologenes*, *Eubacterium limosum*, *Moorella thermautotrophica*, *Moorella thermoacetica*, *Oxobacter pfennigii*, *Sporomusa ovata*, *Sporomusa silvacetica*, *Sporomusa sphaeroides*, and *Thermoanaerobacter kiuvi*. In a preferred embodiment, the C1-fixing bacterium is *Clostridium autoethanogenum*, *Clostridium ljungdahlii*, or *Clostridium ragsdalei*. In an especially preferred embodiment, the C1-fixing bacterium is *Clostridium autoethanogenum*.

BRIEF DESCRIPTION OF THE DRAWINGS

*nogenum* DSM23693 carrying guide RNA and homology arms for targeting region T1 on the 2,3-bdh gene "C2," and *C. autoethanogenum* DSM23693 carrying guide RNA and homology arms for targeting region T2 on the 2,3-bdh gene "C3." Eight colonies carrying two plasmids with cas9, carrying guide RNA and homology arms for targeting region T2 were screened for deletion in the 2,3-bdh gene (lanes marked 1-8).

DETAILED DESCRIPTION OF THE INVENTION

Figure 1A:
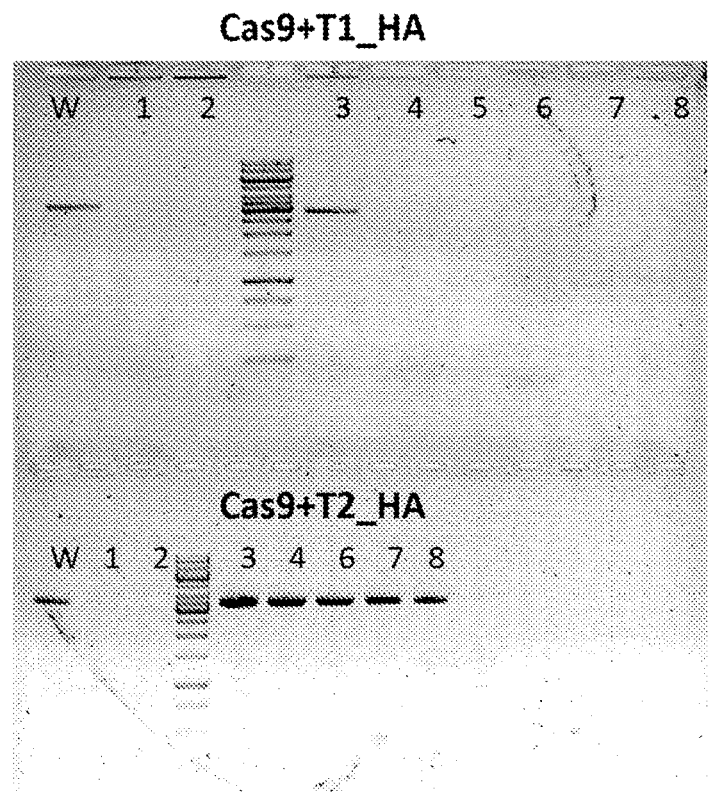
FIG. 1A and FIG. 1B are gel images showing colony PCR for screening deletions in a *C. autoethanogenum* secAdh gene. All colonies carried cas9 gene except for control "W", which is wild-type (unmodified) *C. autoethanogenum* DSM23693. Colonies in rows labelled "Cas9+T1_HA" carried the spacer for target T1 and colonies in rows labelled "Cas9+T2_HA" carried the spacer for target T2.

The inventors have developed a new CRISPR/Cas system suitable for use in C1-fixing bacteria after discovering that existing systems, which rely on Cas9 under the control of a constitutive promoter, are toxic to such bacteria. In particular, attempts to transform the C1-fixing bacterium *C. autoethanogenum* with a plasmid carrying cas9 under the control of a native constitutively-expressed phosphotransacetylase-acetate kinase ($P_{pta-ack}$) promoter were not successful. The CRISPR/Cas system of the invention utilizes an inducible promoter, instead of a constitutive promoter, which renders it suitable for use in C1-fixing bacteria.

In most eukaryotes, double stranded breaks (DSB) are repaired by non-homologous end joining method (NHEJ) (Mali, *Science*, 339: 823-826, 2013; Cong, *Science*, 339: 819-823, 2013). However, in prokaryotes, the repair is by homologous recombination and is mediated by a DNA repair or template or homology arms (HA). CRISPR/Cas9 mediated genome modification has been shown in a diverse array of microbial systems including saccharolytic Clostridia (Xu, *Appl Environ Microbiol*, 81: 4423-4431, 2015; Wang, *J Biotechnol*, 200: 1-5, 2015), but not in C1-fixing bacteria, since, as the inventors have discovered, C1-fixing bacteria require significant modifications in the design of CRISPR/Cas9 tool such as controlled expression of cas9.

The terms "non-naturally occurring" or "engineered" are used interchangeably and indicate the involvement of the hand of man. For example, a genetically engineered microorganism may comprise a genome or other nucleic acids that have been modified (e.g., deleted, mutated, inserted, blocked, silenced, or overexpressed) compared to a non-engineered or naturally-occurring microorganism. As another example, an engineered CRISPR/Cas system may comprise a guide RNA or an inducible promoter that is not present in a non-engineered or naturally-occurring CRISPR/Cas system.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention, the terms "chimeric RNA," "chimeric guide RNA," "guide RNA," "single guide RNA," and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products." "Altering expression" refers to changing the expression of a gene product, e.g., increasing, decreasing, or eliminating the expression of the gene product compared to an unmodified or parental microorganism.

The terms "polypeptide", "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme.

Introduction of a disruptive mutation results in a microorganism of the invention that produces no gene product or substantially no gene product or a reduced amount of gene product compared to the parental microorganism from which the microorganism of the invention is derived. For example, the microorganism of the invention may produce no gene product or at least about 1%, 3%, 5%, 10%, 20%, 30%, 40%, 50%, 60%, 70%, 80%, 90%, or 95% less gene product than the parental microorganism.

"Endogenous" or "homologous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" or "heterologous" refers to a nucleic acid or protein that is not present in the wild-type or parental microorganism from which the microorganism of the invention is derived. In one embodiment, an exogenous gene or enzyme may be derived from a heterologous (i.e., different) strain or species and introduced to or expressed in the microorganism of the invention. In another embodiment, an exogenous gene or enzyme may be artificially or recombinantly created and introduced to or expressed in the microorganism of the invention.

"Codon optimization" refers to the mutation of a nucleic acid, such as a gene encoding a Cas protein such as Cas9, for optimized or improved translation of the nucleic acid in a particular strain or species. Codon optimization may result in faster translation rates or higher translation accuracy. In a preferred embodiment, the genes of the invention are codon optimized for expression in *Clostridium*, particularly *Clostridium autoethanogenum*, *Clostridium ljungdahlii*, or *Clostridium ragsdalei*. In a further preferred embodiment, the genes of the invention are codon optimized for expression in *Clostridium autoethanogenum* LZ1561, which is deposited under DSMZ accession number DSM23693.

"Overexpression" refers to an increase in expression of a nucleic acid or protein in the microorganism of the invention compared to the wild-type or parental microorganism from which the microorganism of the invention is derived.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are well known in the art (e.g., Tijssen, Laboratory techniques in biochemistry and molecular biology-hybridization with nucleic acid probes, Second Chapter "Overview of principles of hybridization and the strategy of nucleic acid probe assay," Elsevier, N.Y, 1993).

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. For example, the promoter may be a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

Typically, in the method of the invention, Cas 9 is under the control of an inducible promoter. The inducible promoter may be, for example, a tetracycline inducible promoter, such as tet3no or ipl12, or a lactose inducible promoter.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes* or *Streptococcus thermophilus*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as a DNA or RNA polynucleotide.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes, S. thermophilus*, or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

As a further example, two or more catalytic domains of Cas9 (RuvC I, RuvC II, and RuvC III) may be mutated to produce a mutated Cas9 substantially lacking all DNA cleavage activity (catalytically inactive). In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP, and Maq. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin.

"Homologous recombination" is a type of genetic recombination in which nucleotide sequences are exchanged between two similar or identical molecules of DNA. In particular, homologous recombination can be used to replace DNA located between homology arms on a vector construct with DNA located between the homology arm targets in a host cell. The homology arms preferably have 100% complementarity to target regions in the host cell. However, the homology arms may have less than 100% complementarity to target regions in the host cell, as long as they have sufficient complementarity to allow for homologous recombination.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010 with Deutsche Sammlung von Mikroorganismen and Zellkulturen GmbH (DSMZ) located at Inhoffenstraß 7B, D-38124 Braunschwieg, Germany on Jun. 7, 2010 under the terms of the Budapest Treaty and accorded accession number DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*,

*Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph. Table 1 provides a representative list of microorganisms and identifies their functional characteristics.

synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is

TABLE 1

|  | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/− [1] | − | − | − |
| *Alkalibaculum bacchii* | + | + | + | + | + | + | − |
| *Blautia producta* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/− [2] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | − [3] | + | + | − |
| *Oxobacter pfennigii* | + | + | + | − | + | + | − |
| *Sporomusa ovata* | + | + | + | − | + | +/− [4] | − |
| *Sporomusa silvacetica* | + | + | + | − | + | +/− [5] | − |
| *Sporomusa sphaeroides* | + | + | + | − | + | +/− [6] | − |
| *Thermoanaerobacter kiuvi* | + | + | + | − | + | − | − |

[1] *Acetobacterium woodi* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

More broadly, the microorganism of the invention may be derived from any genus or species identified in Table 1.

In a preferred embodiment, the microorganism of the invention is derived from the cluster of Clostridia comprising the species *Clostridium autoethanogenum, Clostridium ljungdahlii*, and *Clostridium ragsdalei*. These species were first reported and characterized by Abrini, *Arch Microbiol*, 161: 345-351, 1994 (*Clostridium autoethanogenum*), Tanner, Int J System Bacteriol, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum, Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum, Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), 0-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the invention. Typically, the substrate is gaseous and comprises a C1-carbon source, for example, $CO$, $CO_2$, and/or $CH_4$. Preferably, the substrate comprises a C1-carbon source of $CO$ or $CO+CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % H2. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen (02) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152).

EXAMPLES

The following examples further illustrate the invention but, of course, should not be construed to limit its scope in any way.

Example 1

This example demonstrates culturing of *C. autoethanogenum* DSM23693.

*C. autoethanogenum* DSM23693 (a derivate of DSM10061) was obtained from DSMZ (The German Collection of Microorganisms and Cell Cultures, Inhoffenstraße 7B, 38124 Braunschweig, Germany). Growth was carried out at 37° C. using strictly anaerobic conditions and techniques (Hungate, *Meth Microbiol*, 3B: 117-132, 1969; Wolfe, *Adv Microb Physiol*, 6: 107-146, 1971). Chemically defined PETC medium without yeast extract was used. A 30 psi gas mix (44% CO, 32% $N_2$, 22% $CO_2$, 2% $H_2$) was used as substrate for autotrophic growth. For solid media, 1.2% bacto agar (BD, Franklin Lakes, N.J. 07417, USA) was added.

| PETC medium | Per 1.0 L of medium |
| --- | --- |
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Resazurin (2 g/L stock) | 0.5 ml |
| $NaHCO_3$ | 2 g |
| Reducing agent solution | 0.006-0.008% (v/v) |
| Distilled water | Up to 1.0 L |
| | pH 5.5 (adjusted with HCl) |

| Wolfe's vitamin solution | Per 1.0 L of solution |
| --- | --- |
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |
| Vitamin B12 | 0.1 mg |
| p-Aminobenzoic acid | 5 mg |
| Lipoic acid | 5 mg |
| Thiamine | 5 mg |
| Distilled water | To 1.0 L |

| Trace metal solution | Per 1.0 L of solution |
| --- | --- |
| Nitrilotriacetic acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1.0 L |

| Reducing agent solution | Per 100 mL of solution |
| --- | --- |
| NaOH | 0.9 g |
| Cysteine•HCl | 4 g |
| $Na_2S$ | 4 g |
| Distilled water | To 100 mL |

Example 2

This example demonstrates the deletion of a secondary alcohol dehydrogenase gene (secAdh) in *C. autoethanogenum* DSM23693 using CRISPR/Cas9.

The cas9 gene from *Streptococcus pyogenes* (NC_002737.2 nucleic acid sequence; NP_269215.1 amino acid sequence) was codon adapted to *C. autoethanogenum* DSM23693 and cloned into vector pLZtet3no between NdeI and HindIII restriction endonuclease sites to form vector pLZtet3no-cas9. The expression of cas9 was placed under the control of an inducible promoter.

Two spacers for the *C. autoethanogenum* secondary alcohol dehydrogenase gene (secAdh) (CAETHG_0053; CP006763.1 nucleic acid sequence; AGY74782.1 amino acid sequence) were designed by GenScript. The spacers were synthesized and cloned into vector pMTL83557 between NdeI and PvuII sites to form vectors pMTL83557-secAdh-T1 and pMTL83557-secAdh-T2. The β-lactamase antibiotic selection marker in pMTL83557-secAdh-T1 and pMTL83557-secAdh-T2 was replaced with a chloramphenicol acetyltransferase (catP) antibiotic selection marker to form vectors pMTL83157-secAdh-T1 and pMTL83157-secAdh-T2. The ~1 kb 5' and 3' homology arms of secAdh were PCR amplified from *C. autoethanogenum* DSM23693 genomic DNA using primers 5-HAf3/5-HAr2 and 3-HAf2/3-HAr and KAPA polymerase (BioRad).

Genomic DNA was isolated using a modified method by Bertram, *Arch Microbiol*, 151: 557-557, 1989. A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 μl lysozyme (100,000 U) was added and the mixture was incubated at 37°

C. for 30 min, followed by addition of 280 µl of a 10% (w/v) SDS solution and another incubation for 10 min. RNA was digested at room temperature by addition of 240 µl of an EDTA solution (0.5 M, pH 8), 20 µl Tris-HCl (1 M, pH 7.5), and 10 µl RNase A (Fermentas Life Sciences). Then, 100 µl Proteinase K (0.5 U) was added and proteolysis took place for 1-3 h at 37° C. Finally, 600 µl of sodium perchlorate (5 M) was added, followed by a phenol-chloroform extraction and an isopropanol precipitation. DNA quantity and quality was inspected spectrophotometrically.

The homology arms were cloned into vectors pMTL83157-secAdh-T1 and pMTL83157-secAdh-T2 using a GeneArt seamless cloning kit. The vector backbone for seamless cloning was PCR amplified using primers BBf2/BBr2 and KAPA polymerase. The resulting vectors are referred as pMTL83157-secAdh-T1-HA and pMTL83157-secAdh-T2-HA.

Vector pLZtet3no-cas9 was transformed into C. autoethanogenum DSM23693 via conjugation. For this, the expression vector was first introduced into the conjugative donor strain E. coli HB101+R702 (CA434) (Williams, J Gen Microbiol, 136: 819-826) (the donor) using standard heat shock transformation. Donor cells were recovered in SOC medium (Sambrook, Molecular cloning: A laboratory manual, Vol 3, Cold Spring Harbour Press, 1989) at 37° C. for 1 h before being plated on to LB medium (Sambrook, Molecular cloning: A laboratory manual, Vol 3, Cold Spring Harbour Press, 1989) plates containing 100 µg/ml spectinomycin and 25 µg/ml chloramphenicol. LB plates were incubated at 37° C. overnight. The next day, 5 ml LB aliquots containing 100 µg/ml spectinomycin and 25 µg/ml chloramphenicol were inoculated with several donor colonies and incubated at 37° C., shaking for approximately 4 h, or until the culture was visibly dense but had not yet entered stationary phase. 1.5 ml of the donor culture was harvested in a microcentrifuge tube at room temperature by centrifugation at 4000 rpm for 2 min, and the supernatant was discarded. The donor cells were gently resuspended in 2 ml sterile PBS buffer (Sambrook, Molecular cloning: A laboratory manual, Vol 3, Cold Spring Harbour Press, 1989) and centrifuged at 4000 rpm for 5 min and the PBS supernatant was discarded. The pellet was introduced into an anaerobic chamber and gently resuspended in 200 µl during late exponential phase C. autoethanogenum culture (the recipient). The conjugation mixture (the mix of donor and recipient cells) was spotted onto PETC-MES agar plates and left to dry. When the spots were no longer visibly wet, the plates were introduced into a pressure jar, pressurized with syngas to 25-30 psi and incubated at 37° C. for ~24 h. After 24 h incubation, the conjugation mixture was removed from the plates by gently scraping it off using a 10 µl inoculation loop. The removed mixture was suspended in 200-300 µl PETC medium. 100 µl aliquots of the conjugation mixture were plated on to PETC medium agar plates supplemented 5 µg/ml clarithromycin to select for transformants bearing the pLZtet3no-cas9 vector and 10 µg/ml trimethoprim to counter select E. coli.

Three distinct colonies, or clones, of C. autoethanogenum DSM23693 bearing the pLZtet3no-cas9 vector were inoculated into 2 mL of PETC-MES medium with 5 µg/ml clarithromycin and grown autotrophically at 37° C. with 100 rpm orbital shaking for three days. One clone of C. autoethanogenum DSM23693 bearing the pLZtet3no-cas9 was transformed with the second plasmid pMTL83157-secAdh-T1_HA or pMTL83157-secAdh-T2_HA as explained above. The transformants were selected on PETC agar medium containing 5 µg/ml clarithromycin, 10 µg/ml trimethoprim and 15 µg/ml thiamphenicol. Colonies were streaked on PETC agar plates containing all 3 antibiotics and 32 ng/µl anhydrotetracycline to induce the expression of cas9. From the resulting colonies, 8 were screened for deletion in secAdh gene by PCR using primers SNsc-CR-09/OgAM58 and KAPA polymerase. The unmodified C. autoethanogenum DSM23693 would amplify a product of 3382 bp and mutants with deletion of 891 bp fragment within the secAdh gene and between the homology arms would amplify a product of 2491 bp.

Figure 1B:
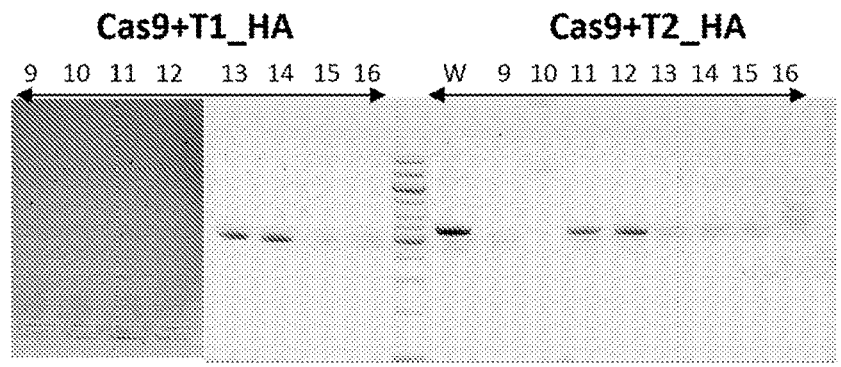
Figure 1C:
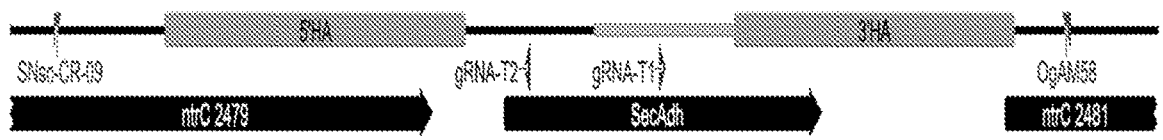
FIG. 1C is a diagram showing the secAdh locus with homology arms 5'HA and 3'HA, primers SNscCR-09 and OgAM58 used for screening, and the spacer targeting region gRNA-T1 and gRNA-T2 within the secAdh gene. The fragment of secAdh that was deleted due to the activity of the CRISPR/Cas9 system is marked (between the 5' and 3' homology arms).

Three clones containing cas9+T1_HA had a truncated secAdh gene (FIG. 1A and FIG. 1B) with 466 bp deletion at the 3' end of the gene (FIG. 1C). This was confirmed by Sanger sequencing of the PCR product. None of the clones containing cas9+T2_HA had any modification in the secAdh gene (FIG. 1A and FIG. 1B). In this example, the efficiency of CRISPR-II/Cas9 to make gene deletions in C. autoethanogenum appears to be ~20%. This clearly shows that the CRISPR-II/Cas9 system from Streptococcus pyogenes is functional in C. autoethanogenum.

Example 3

This example demonstrates the deletion of a 2,3-butanediol dehydrogenase (2,3-bdh) gene in C. autoethanogenum DSM23693 using CRISPR/Cas9.

To further optimize the CRISPR/Cas9 system for better efficiency in C. autoethanogenum, the expression of cas9 gene was put under the control of a stronger tetracycline inducible promoter, ipl12. Additionally, the homology arms were designed to be within 100 bp from Cas9 cleavage site.

Figure 2A:
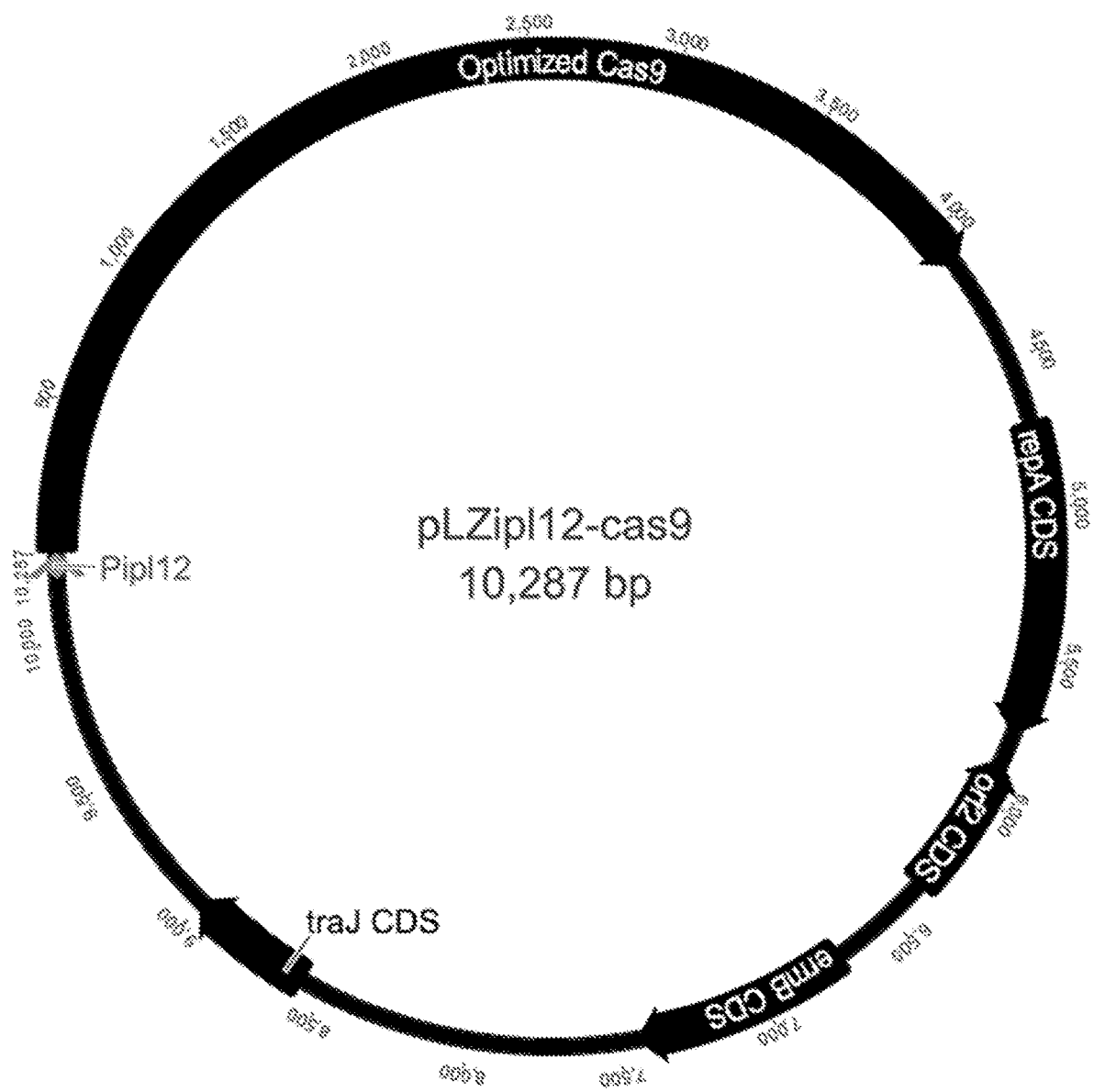
FIG. 2A is a map of plasmid pLZipl12-cas9 where the expression of the cas9 gene is controlled by a strong tetracycline inducible promoter Pipl12. The guide RNA and the homology arms for the target gene were introduced into *C. autoethanogenum* DSM23693 on a second plasmid.

The cas9 gene from pLZtet3no-cas9 was cloned into pLZipl12 plasmid between NdeI and HindIII sites to form plasmid pLZipl12-cas9 (FIG. 2A). The pIPL12 has a stronger tetracycline inducible promoter compared to pLZtet3no.

Figure 2B:
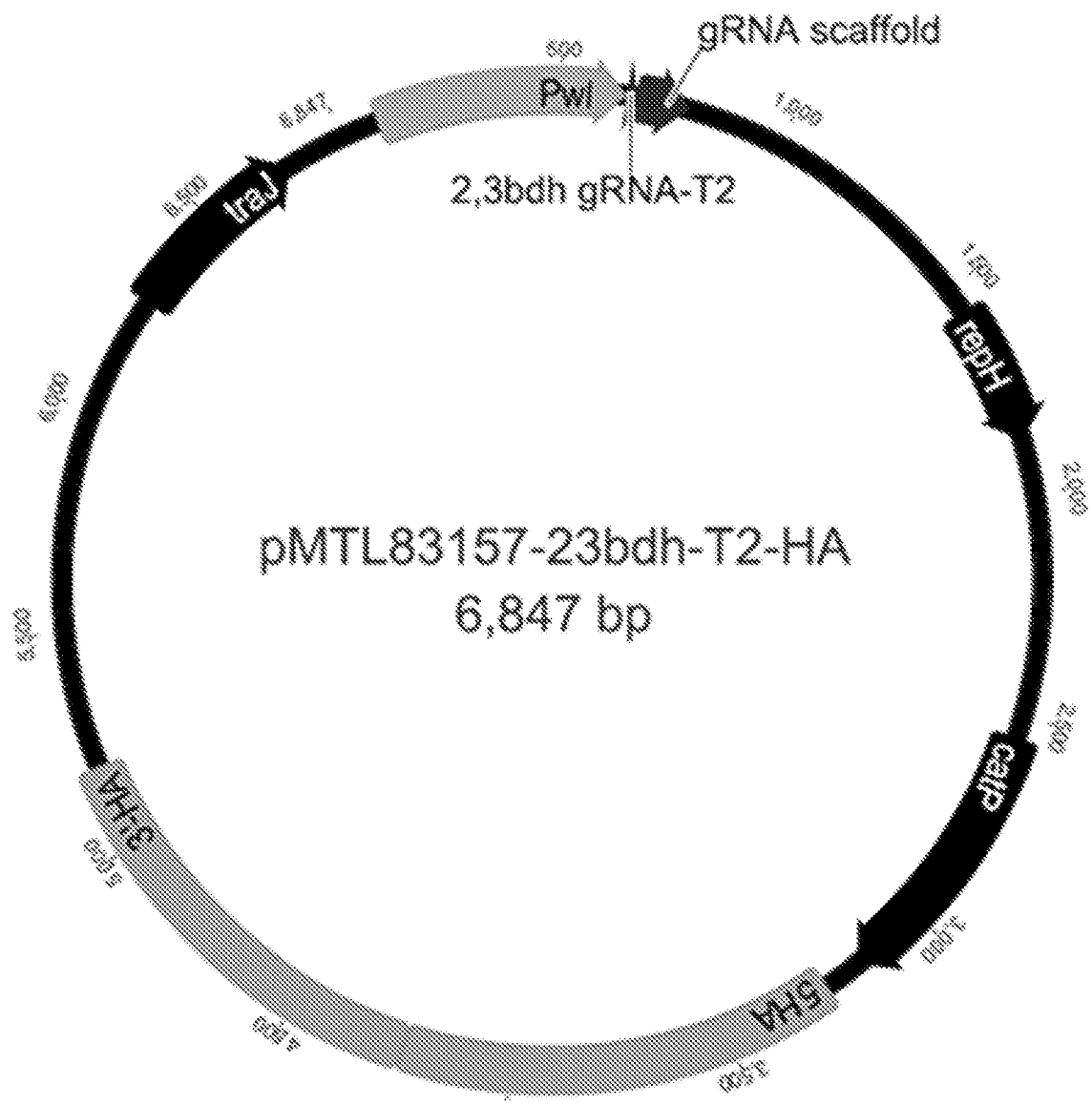
FIG. 2B is a map of an example plasmid carrying guide RNA against the 2,3-bdh gene along with the homology arms for the 2,3-bdh gene.

Two spacers for a C. autoethanogenum 2,3-butanediol dehydrogenase gene (CAETHG_0385; CP006763.1 nucleotide sequence; AGY74614.1 amino acid sequence) were designed by GenScript. The spacers were cloned into pMTL83557 between NdeI and PvuII sites to form vectors pMTL83557-2,3bdh-T1 and pMTL83557-2,3bdh-T2. The β-lactamase antibiotic selection marker in pMTL83557-2,3bdh-T1 and pMTL83557-2,3bdh-T2 (FIG. 2B) was replaced with chloramphenicol acetyltransferase (catP) antibiotic selection marker to get vectors pMTL83157-2,3bdh-T1 and pMTL83157-2,3bdh-T2. The ~1 kb 5' and 3' homology arms flanking 2,3bdh gene were PCR amplified from C. autoethanogenum DSM23693 genomic DNA using primers SNr05f/SNr06r and SNr07f/SNr08r and KAPA polymerase (BioRad). The homology arms were ~70 bp from the Cas9 cleavage site. The two PCR products were spliced by PCR using primers SNr05f/SNr08r which include PmeI restriction site. The resulting ~2 kb PCR product was cloned into vectors pMTL83157-2,3bdh-T1 and pMTL83157-2,3bdh-T2 between PmeI restriction site to obtain vectors pMTL83157-2,3bdh-T1¬_HA and pMTL83157-2,3bdh-T2_HA.

The vectors, pLZipl12-cas9, pMTL83157-2,3bdh-T1_HA, and pMTL83157-2,3bdh-T2_HA were transformed into C. autoethanogenum DSM23693 via conjugation as explained above. One clone obearing the pLZipl12-cas9 was transformed with the second plasmid pMTL83157-2,3bdh-T1_HA or pMTL83157-2,3bdh-T2_HA as explained above. The transformants were selected on PETC agar medium containing 5 µg/ml clarithromycin, 10 µg/ml trimethoprim and 15 µg/ml thiamphenicol. Colonies were observed only with pLZipl12-cas9 and pMTL83157-2,3bdh-T2_HA. From this, 8 colonies were streaked on PETC agar plates containing all 3 antibiotics and 32 ng/µl anhydrotetracycline to induce the expression of the Cas9 gene.

Figure 3A:
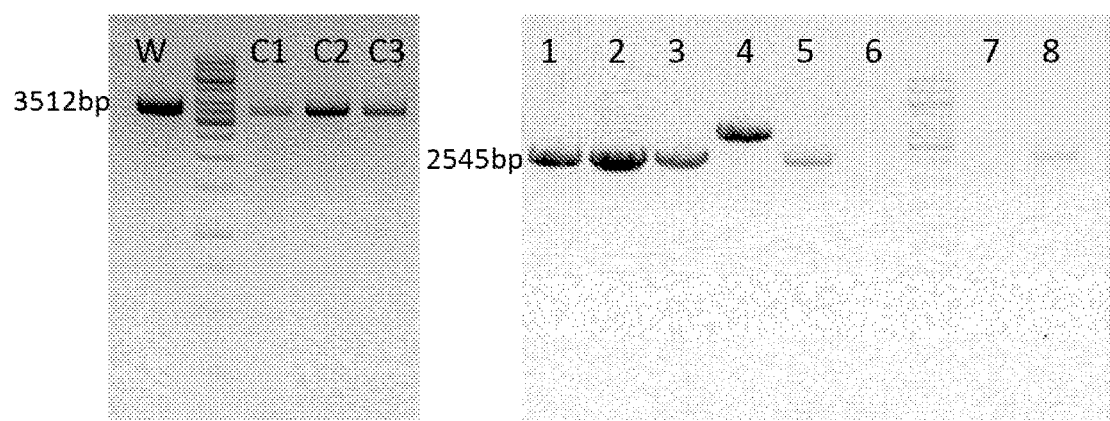
FIG. 3A is a gel image showing colony PCR for screening deletions in a *C. autoethanogenum* 2, 3-bdh gene using primers Og33f and Og34r. Wild-type (unmodified) *C. autoethanogenum* DSM23693 "W", *C. autoethanogenum* DSM23693 carrying the cas9 gene only "C1", *C. autoetha-*
Figure 3B:
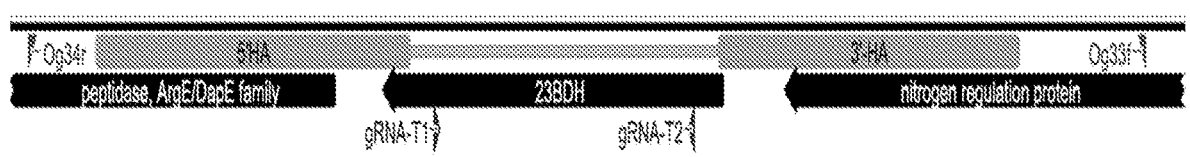
FIG. 3B is a diagram showing the 2,3-bdh locus with homology arms 5'HA and 3'HA, the primers Og33f and Og34r used for screening, and the spacer targeting region gRNA-T1 and gRNA-T2 within the 2,3-bdh gene. The fragment of 2,3-bdh that is deleted due to the activity of the CRISPR/Cas9 system is located between the homology arms.

The resulting colonies were screened for deletion in the 2,3-bdh gene by PCR using primers Og33f/Og34r and KAPA polymerase. The unmodified *C. autoethanogenum* DSM23693 would amplify a product of 3512 bp and mutants with deletion of 967 bp fragment within the 2,3-bdh gene and between the homology arms would amplify a product of 2545 bp. While 3512 bp fragment was amplified from unmodified *C. autoethanogenum* DSM23693 and *C. autoethanogenum* DSM23693 carrying either pLZipl12-cas9 or pMTL83157-2,3bdh-T1_HA or pMTL83157-2, 3bdh-T2_HA alone (FIG. 3A, lanes W, C1, C2 and C3), deletion of 967 bp fragment within the 2,3-bdh gene was observed in 5 out of 8 clones carrying the 2 vectors pLZipl12-cas9 and pMTL83157-2,3bdh-T2_HA (FIG. 3A, lanes 1-8, and FIG. 3B). The deletion was further confirmed by Sanger sequencing of the PCR products.

The use of a stronger tetracycline inducible promoter to drive Cas9 gene expression and proximity of 3'-homology arm close to the Cas9 cleavage site within spacer-2 of 2,3-bdh appears to have improved the efficiency of CRISPRii-cas9 system in *C. autoethanogenum* to 60%.

Example 4

This example demonstrates the deletion of a 2,3-butanediol dehydrogenase (2,3-bdh) gene in *C. autoethanogenum* DSM23693 using a nickase version of cas9 and an alternative plasmid design.

To increase the efficiency of the CRISPR/Cas9 system and to reduce the number of transformation steps from two (as in the above Examples) to one, two modifications were further introduced. The first modification was the use of a nickase version of the cas9 gene.

The second modification was the assembly of all three CRISPR/Cas9 components (nickase cas9, gRNA cassette, and homology arms) on a single plasmid.

The Cas9 nuclease consists of two endonuclease domains, RuvC and HNH. With the mutation of aspartic acid at position-10 to alanine (D10A) in the RuvC domain, the mutant cas9 is known to retain only nickase activity leading to single stranded breaks rather than double stranded breaks introduced by the wild type cas9 enzyme (Jinek, *Science*, 337: 816-821, 2012).

Figure 4:
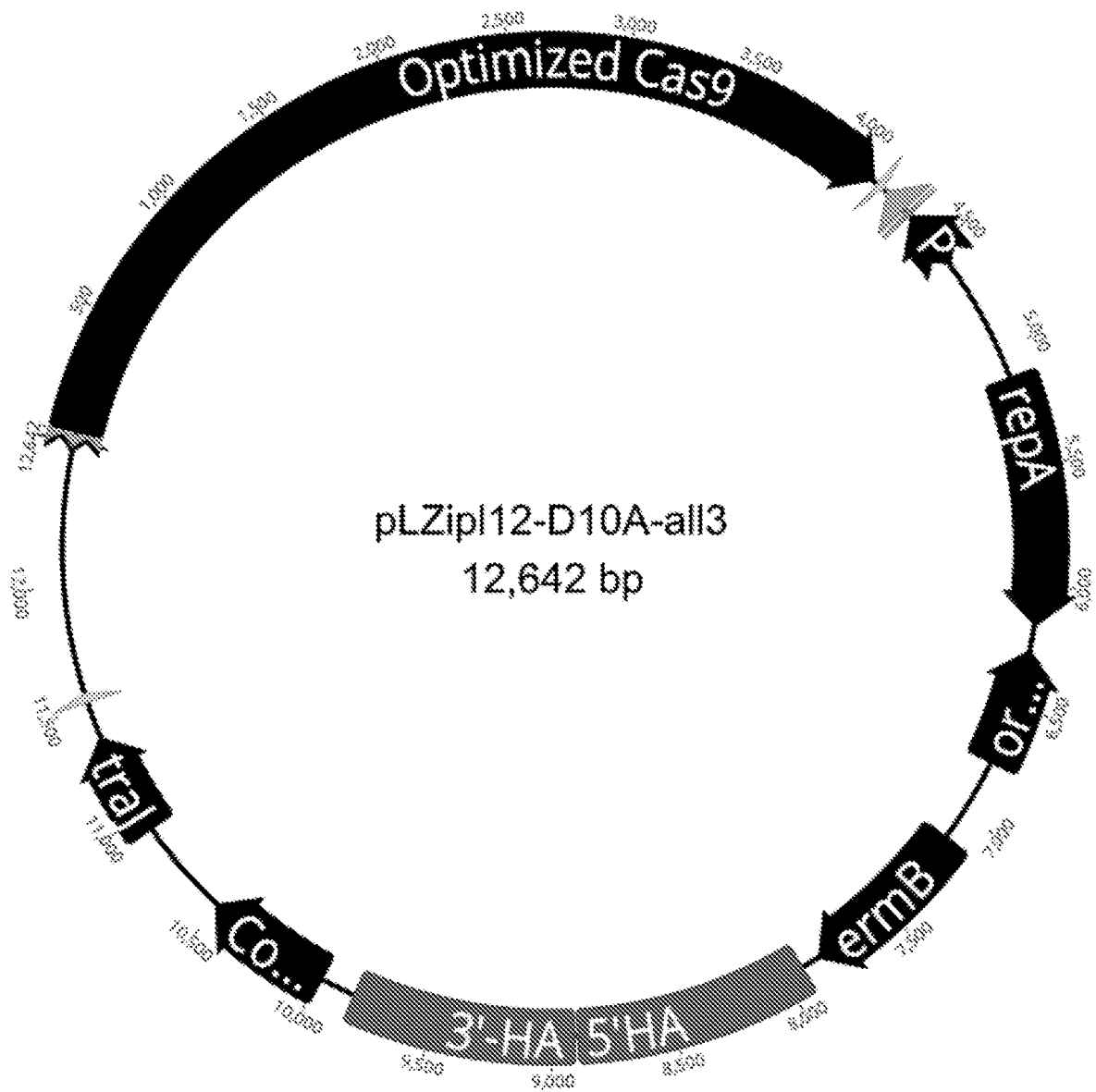
FIG. 4 is a map of plasmid pLZipL12-D10A-all13.

The D10A mutation in pLZipl12-cas9 was introduced using oligonucleotides subsequent to the assembly of 2,3-bdh-gRNA-T1 at AscI site and the homology arms between PmeI site. The resulting plasmid, pLZipl12-D10A-all3 (FIG. 4), was introduced into *C. autoethanogenum* DSM23693 followed by induction of nickase Cas9 expression and screening for 2,3-bdh gene deletion. The gene deletion efficiency was similar to that observed in Example 3. With this design, the transformation step and processing time was further reduced.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of genetically engineering a C1-fixing bacterium comprising introducing into a C1-fixing bacterium containing a DNA molecule comprising a target sequence an engineered, non-naturally occurring Clustered Regularly Interspaced Short Palindromic Repeats (CRISPR)/CRISPR-associated (Cas) (CRISPR/Cas) system comprising one or more vectors comprising:
   (a) a nucleotide sequence encoding a guide RNA that hybridizes with the target sequence and
   (b) a nucleotide sequence encoding a type-II Cas9 protein under the control of an inducible promoter;
   wherein the inducible promoter is ipl12;
   wherein the Cas9 interacts with the DNA molecule; and
   wherein expression of a gene product or a nucleotide sequence of the DNA molecule is altered.

2. The method of claim 1, wherein the CRISPR/Cas system further comprises on the one or more vectors:
   (c) a nucleotide sequence comprising a 5' homology arm that hybridizes upstream of the target sequence and a 3' homology arm that hybridizes downstream of the target sequence,
   whereby the 5' homology arm and the 3' homology arm hybridize with the DNA molecule and homologous recombination occurs, resulting in the replacement of the target sequence with DNA located between the 5' homology arm and the 3' homology arm.

3. The method of claim 2, wherein the DNA located between the 5' homology arm and the 3' homology arm disrupts the DNA molecule, whereby expression of the gene product of the DNA molecule is decreased.

4. The method of claim 2, wherein the DNA located between the 5' homology arm and the 3' homology arm encodes an exogenous gene, whereby the homologous recombination inserts the exogenous gene into the DNA molecule.

5. The method of claim 4, wherein the C1-fixing bacterium expresses the exogenous gene.

6. The method of claim 2, wherein (a), (b), and (c) are located on the same or different vectors.

7. The method of claim 1, wherein the Cas9 is catalytically active.

8. The method of claim 1, wherein the Cas9 is nickase Cas9.

9. The method of claim 1, wherein the Cas9 is catalytically inactive.

10. The method of claim 1, wherein the Cas9 cleaves the DNA molecule and expression of the gene product of the DNA molecule is decreased.

11. The method of claim 1, wherein the Cas9 blocks the DNA molecule and expression of the gene product of the DNA molecule is decreased.

12. The method of claim 1, wherein (a) and (b) are located on the same or different vectors.

13. The method of claim 1, wherein the CRISPR/Cas system is derived from *Streptococcus pyogenes* or *Streptococcus thermophilus*.

14. The method of claim 1, wherein the C1-fixing bacterium is selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kiuvi*.

15. The method of claim 1, wherein the C1-fixing bacterium is *Clostridium autoethanogenum, Clostridium ljungdahlii,* or *Clostridium ragsdalei*.

16. The method of claim 1, wherein the C1-fixing bacterium is *Clostridium autoethanogenum*.

* * * * *